(12) United States Patent
Sharma et al.

(10) Patent No.: US 12,018,096 B2
(45) Date of Patent: Jun. 25, 2024

(54) POTENT PEPTIDE INHIBITORS OF PROTEIN AGGREGATION

(71) Applicant: COUNCIL OF SCIENTIFIC & INDUSTRIAL RESEARCH, New Delhi (IN)

(72) Inventors: Deepak Kumar Sharma, Chandigarh (IN); Arpit Gupta, Chandigarh (IN); Gajendra Pal Singh Raghava, New Delhi (IN); Gautam Ankur, Chandigarh (IN); Manisha Kumari, Chandigarh (IN)

(73) Assignee: COUNCEL OF SCIENTIFIC & INDUSTRIAL RESEARCH, New Delhi (IN)

( * ) Notice: Subject to any disclaimer, the term of this patent is extended or adjusted under 35 U.S.C. 154(b) by 801 days.

(21) Appl. No.: 16/647,149

(22) PCT Filed: Sep. 20, 2018

(86) PCT No.: PCT/IN2018/050610
§ 371 (c)(1),
(2) Date: Mar. 13, 2020

(87) PCT Pub. No.: WO2019/058389
PCT Pub. Date: Mar. 28, 2019

(65) Prior Publication Data
US 2023/0212224 A1 Jul. 6, 2023

(30) Foreign Application Priority Data
Sep. 20, 2017 (IN) .............................. 201711033280

(51) Int. Cl.
*C07K 7/08* (2006.01)
*A61K 38/00* (2006.01)
*C12N 15/10* (2006.01)
*C12P 21/02* (2006.01)

(52) U.S. Cl.
CPC ............ *C07K 7/08* (2013.01); *C12N 15/1055* (2013.01); *C12P 21/02* (2013.01); *A61K 38/00* (2013.01)

(58) Field of Classification Search
CPC ....... C07K 7/08; C12N 15/1055; C12P 21/02; A61K 38/00
See application file for complete search history.

(56) References Cited

U.S. PATENT DOCUMENTS

| 2013/0029358 A1* | 1/2013 | Valmori | ........... G01N 33/56972 530/300 |
| 2015/0337279 A1* | 11/2015 | Zhang | .................. C12N 9/2437 435/189 |
| 2016/0222072 A1* | 8/2016 | Gao | ....................... C07K 14/47 |

FOREIGN PATENT DOCUMENTS

| WO | 0107442 A1 | 2/2001 | |
| WO | 2004009625 A2 | 1/2004 | |
| WO | 2007145589 A1 | 12/2007 | |
| WO | 2008003943 A2 | 1/2008 | |
| WO | WO 2009/117480 | * 9/2009 | ............... C07K 7/06 |
| WO | WO 2010/129023 | * 11/2010 | ............ C07K 14/00 |
| WO | 2014184596 A2 | 11/2014 | |

OTHER PUBLICATIONS

Prusiner, Stanley B. "Prions." Proc. Natl. Acad. Sci. USA, vol. 95, pp. 13363-13383, Nov. 1998 (Nobel Lecture).
Sunde, Margaret and Blake, Colin C.F. "From the globular to the fibrous state: protein structure and structural conversion in amyloid formation." Quarterly Reviews of Biophysics 31, 1(1998), pp. 1-39.
Spillantini, Maria Grazia et al. "α-Synuclein in Lewy bodies" Nature, vol. 388, Aug. 28, 1997, pp. 839-840.
Spillianatini, Maria Grazia et al. "α-Synuclein in filamentous inclusions of Lewy bodies from Parkinson's disease and dementia with Lewy bodies." Proc. Natl. Acad. Sci. USA, vol. 95, pp. 6467-6473, May 1998.
Bucciantini, Monica et al. "Inherent toxicity of aggregates implies a common mechanism for protein misfolding diseases." Nature, vol. 416, Apr. 4, 2002 pp. 507-511.
Wu, Chien-Hsun et al. "Advancement and applications of peptide phage display technology in biomedical science." Journal of Biomedical Science (2015) 23:8, 14 Pages.
Kisilevsky, Robert et al. "Arresting amyloidsis in vivo using small-molecule anionic sulphonates or sulphates: implications for Alzheimer's disease." Nature Medicine, vol. 1, No. 2, Feb. 1995.
Wood, Stephen J. et al. "Selective Inhibition of Aβ Fibrile Formation." The Journal of Biological Chemistry, vol. 271, No. 8, Issue of Feb. 23, 1996, pp. 4086-4092.
Perni, Michele et al. "A natural product inhibits the initiation of α-synuclein aggregation and suppresses its toxicity." PNAS, Published online Jan. 17, 2017. E1009-E1017.
Caruana, Mario et al. "Polyphenolic compounds are novel protective agents against lipid membrane damage by α-synuclein aggregates in vitro." Biochimica et Biophysica Acta 1818 (2012) 2502-2510.
Cheruvara, Harish et al. "Intracellular Screening of a Peptide Library to Derive a Potent Peptide Inhibitor of α-Synuclein Aggregation." The Journal of Biological Chemistry, vol. 290, No. 12, Mar. 20, 2015, pp. 7426-7435.
Emadi, Sharareh et al. "Inhibiting Aggregation of α-Synuclein with Human Single Chain Antibody Fragments." Biochemistry 2004, 43, 2871-2878.

(Continued)

*Primary Examiner* — Amber D Steele
(74) *Attorney, Agent, or Firm* — Blank Rome LLP (57) ABSTRACT

The present disclosure provides a novel peptide as potent inhibitor of protein aggregation. A peptide for an inhibition of protein aggregation having the general Formula 1, $[X_iSACX_1]_m HHHH[X_2X_3CGG]_m$ (SEQ ID NO. 9) is provided. The m is 0 or 1; $X_i$ is an acetyl group; $X_1$ is a hydrophilic polar uncharged amide group containing amino acid; $X_2$ is His or Leu; and $X_3$ is His or Ser. The present disclosure specifically relates to peptide-based inhibitors useful in treatment of amyloid related disorders.

6 Claims, 5 Drawing Sheets

Specification includes a Sequence Listing.

(56) References Cited

OTHER PUBLICATIONS

Singh, Pradeep K. et al. "Curcumin Modulates α-Synuclein Aggregation and Toxicity." ACS Publications. ACS Chem. Neurosci. 2013, 4, 393-407.

Bieschke, Jan et al. "EGCG remodels mature α-synuclein and amyloid-ß fibrils and reduces cellular toxicity." PNAS, vol. 107, No. 17, Apr. 27, 2019. pp. 7710-7715.

Gautam, Ankur et al. "Identification and characterization of novel protein-derived arginine-rich cell-penetrating peptides." European Journal of Pharmaceutics and Biopharmaceutics, 89 (2015) 93-106.

Van Raaij, Martijn E. et al. "Quantitative Morphological Analysis Reveals Ultrastructural Diversity of Amyloid Fibrils from α-Synuclein Mutants." Biophysical Journal: Biophysical Letters . 2006. 3 pages.

* cited by examiner

POTENT PEPTIDE INHIBITORS OF PROTEIN AGGREGATION

CROSS REFERENCE TO RELATED APPLICATIONS

This application is a national phase of International Application No. PCT/IN2018/050610 filed Sep. 20, 2018 and claims priority from Indian Patent Application No. 201711033280 filed Sep. 20, 2017, both incorporated by reference in their entirety.

SEQUENCE LISTING

The instant application contains a Sequence Listing which has been submitted electronically in ASCII format and is hereby incorporated by reference in its entirety. Said ASCII copy, created on Jun. 20, 2023, is named 134839-00156_SL.txt and is 4,286 bytes in size.

FIELD OF THE INVENTION

This invention relates to a novel peptide having general Formula 1 having ability to inhibit protein aggregation. More precisely a novel peptide to inhibit the process of conversion of intrinsically disordered proteins such as α-synuclein (α-syn) into β-sheet rich fibrils, and thus could be used as potent lead molecule for the treatment of various neurodegenerative diseases such as Parkinson's disease (PD), Alzheimer's disease (AD), Huntington's disease (HD), diabetes and α-synucleinopathies.

BACKGROUND OF THE INVENTION

Neurodegenerative disorders forms a class of disorders associated with impaired functionality of neurons. Many of the neurodegenerative diseases are characterized by the accumulation of β-sheet rich amyloids. Apart from neurodegenerative disorders amyloids are also associated with Diabetes. Though proteins involved in these diseases (Aβ in AD, α-Syn in PD, Huntingtin in HD, SOD1 in ALS and PrP in prion diseases) have discrete primary sequence and are unrelated, they all undergo a similar conformational transition to form amyloids that share several conserved structural and biochemical properties such as high β-sheet content and SDS-insolubility (Prusiner, S. B. (1998). Prions. Proceedings of the National Academy of Sciences 95, 13363-13383; Sunde, M., and Blake, C. C. F. (1998). From the globular to the fibrous state: protein structure and structural conversion in amyloid formation. Quarterly Reviews of Biophysics 31, 1-39). Currently, these diseases are non-curable and fatal. The mechanism through which amyloid formation causes neurotoxicity is not clearly understood.

The current study focuses on the development of inhibitors of fibrillation formed by various intrinsically disordered proteins. The intrinsically disordered protein α-syn was used as model protein to identify such inhibitors. The α-syn is known to form amyloid fibrils and the deposition of such protein inclusions in cells leads to cytotoxicity which is associated with not only PD, but also many diseases collectively known as α-Synucleinopathies (Spillantini, M. G., Schmidt, M. L., Lee, V. M. Y., Trojanowski, J. Q., Jakes, R., and Goedert, M. (1997). [alpha]-Syn in Lewy bodies. Nature 388, 839-840; Spillantini, M. G., Crowther, R. A., Jakes, R., Hasegawa, M., and Goedert, M. (1998). α-Syn in filamentous inclusions of Lewy bodies from Parkinson's disease and dementia with Lewy bodies. Proceedings of the National Academy of Sciences 95, 6469-6473). According to Centre for Disease Control (CDC) report, PD is the 14$^{th}$ leading cause of death in US (National Vital Statistics Report, 2014). PD is caused due to death of dopaminergic neurons, which are responsible for controlling muscle activity. The key pathological feature of PD is accumulation of abnormal aggregate of proteins known as lewy bodies.

The α-syn is the main component of lewy bodies deposited in dopaminergic neurons of PD patients. α-Syn is a member of the Syn family of proteins abundantly present in pre-synaptic terminals of neuronal tissues. The Syn members are characterized by the presence of 5 or 6 imperfect repeats of motif KTKEGV (SEQ ID NO: 12) at the N-terminus, a central hydrophobic non-amyloid beta component (NAC) domain and an acidic carboxy terminal tail. It is believed that the protofibrils that are formed during conformational transition of native α-syn into fibrils cause toxicity (Bucciantini, M., Giannoni, E., Chiti, F., Baroni, F., Formigli, L., Zurdo, J., Taddei, N., Ramponi, G., Dobson, C. M., and Stefani, M. (2002). Inherent toxicity of aggregates implies a common mechanism for protein misfolding diseases. Nature 416, 507-511), and thus strategies to block the process of fibrillation would lead to effective therapeutics against amyloid based disorders. Previously many groups have contributed towards finding a potent inhibitor of α-syn aggregation (Wu, C.-H., Liu, I.-J., Lu, R.-M., and Wu, H.-C. (2016). Advancement and applications of peptide phage display technology in biomedical science. Journal of Biomedical Science 23, 8; Kisilevsky, R., Lemieux, L. J., Fraser, P. E., Kong, X., Hultin, P. G., and Szarek, W. A. (1995). Arresting amyloidosis in vivo using small-molecule anionic sulphonates or sulphates: implications for Alzheimer's disease. Nat Med 1, 143-148; Wood, S. J., MacKenzie, L., Maleeff, B., Hurle, M. R., and Wetzel, R. (1996). Selective Inhibition of A Fibril Formation. Journal of Biological Ckhemistry 271, 4086-4092; Perni, M., Galvagnion, C., Maltsev, A., Meisl, G., Müller, M. B. D., Challa, P. K., Kirkegaard, J. B., Flagmeier, P., Cohen, S. I. A., Cascella, R., et al. (2017). A natural product inhibits the initiation of α-syn aggregation and suppresses its toxicity. Proceedings of the National Academy of Sciences; Caruana, M., Neuner, J., Hogen, T., Schmidt, F., Kamp, F., Scerri, C., Giese, A., and Vassallo, N. (2012). Polyphenolic compounds are novel protective agents against lipid membrane damage by α-syn aggregates in vitro. Biochimica et Biophysica Acta (BBA)—Biomembranes 1818, 2502-2510; Fulop, L., Penke, B., Zarandi, M., Bozso, Z., Virok, D., Janaky, T., Verdier, Y., Datki, Z., Szegedi, V., and Busa-fekete, R. (2015). Small peptide inhibitors of α-amyloid toxicity. (Google Patents); Arvidsson, P., and Johansson, J. (2009). Peptides that are capable of binding to amyloid-beta peptide. (Google Patents); Barnham, K. J., Mccarthy, T. D., Pallich, S., Matthews, B. R., and Cherny, R. A. (2001). Beta-amyloid peptide inhibitors. (Google Patents); Carulla, N., Fowler, S., Giralt, E., Stallwood, Y., Teixido, M., and Zurdo, J. (2008). Inhibition of alpha-syn aggregation. (Google Patents); El-Agnaf, O. M. A., and Allsop, D. (2004). Peptides and peptide derivatives for the treatment of α-synuclein-related diseases. (Google Patents); Cheruvara, H., Allen-Baume, V. L., Kad, N. M., and Mason, J. M. (2015). Intracellular Screening of a Peptide Library to Derive a Potent Peptide Inhibitor of α-Syn Aggregation. Journal of Biological Chemistry 290, 7426-7435; Emadi, S., Liu, R., Yuan, B., Schulz, P., McAllister, C., Lyubchenko, Y., Messer, A., and Sierks, M. R. (2004). Inhibiting Aggregation of α-Syn with Human Single Chain Antibody Fragments. Biochemistry 43, 2871-2878; Singh, P. K., Kotia, V., Ghosh, D., Mohite, G. M., Kumar, A., and Maji, S. K. (2013). Curcumin Modulates α-Syn Aggregation and Toxicity. ACS Chemical Neuroscience 4, 393-407; Bieschke, J., Russ, J., Friedrich, R. P., Ehrnhoefer, D. E., Wobst, H., Neugebauer, K., and Wanker, E. E. (2010). EGCG remodels mature α-syn and amyloid-β fibrils and reduces cellular toxicity. Proceedings of the National Academy of Sciences 107, 7710-7715). None of these molecules has become successful.

Phage display is a powerful method to screen number of peptides against the desired phenotype. Here a peptide or protein is fused with a bacteriophage coat protein and is displayed on a virion surface. Phages display random peptide libraries genetically encoded in phages genome. The peptides displayed phages are further screened against the protein of interest, and the interacting phages separated by affinity purification in the screening process as per manufacturer's protocol (NEB #E8110S). Affinity selection (called biopanning) is used to identify peptides binding to the individual target. The primary structure of the peptide is determined by DNA sequencing of individual clones.

In the present invention, in order to identify potential peptide inhibitors of α-syn fibrillation, we screened commercially available phage display library with cyclic-7 peptides for their ability to interact with α-syn. The identified peptides were further tested for their ability to inhibit α-syn fibrillation.

OBJECT OF THE INVENTION

The main object of the invention is to provide a novel peptide with potential to inhibit fibrillation of intrinsically disordered proteins such as α-syn.

SUMMARY OF THE INVENTION

Accordingly, the present invention pertains to novel peptide which inhibits fibrillation of an intrinsically disordered protein, and thus could be used as potent lead molecule for the treatment of amyloid based disorders such as Parkinson's disease, Alzheimer's disease, Huntington's disease, Diabetes and α-synucleinopathies.

In an embodiment, a peptide for an inhibition of protein aggregation having the general Formula 1, $[X_iSACX_1]_m HHHH[X_2X_3CGG]_m$ (SEQ ID NO: 9) is provided. The m is 0 or 1; $X_i$ is an acetyl group; $X_1$ is a hydrophilic polar uncharged amide group containing amino acid; $X_2$ is His or Leu; and $X_3$ is His or Ser. In another embodiment, the amino acid at C-terminus in the peptide is amidated. The peptide is for treating amyloid associated disorders. The inhibitory activity of the peptide is against β-sheet polymerisation of amyloidogenic proteins. The peptide comprises the amyloidogenic protein which is preferably α-syn.

In one embodiment, a method for preparing the peptide having Formula 1 is provided. The method comprising the steps of: providing $His_6$-tagged α-syn ("His6" disclosed as SEQ ID NO: 11) bound on $Co^{++}$-NTA resin in the range of 4-7 µg; providing a phage library each encoding from $2\times10^{11}$-$7\times10^{11}$ pfu displaying cyclic peptide; characterised in incubating nearly $10^{11}$ titre of the phage library obtained at step b with the $His_6$-tagged α-syn ("His6" disclosed as SEQ ID NO: 11) bound on $Co^{++}$-NTA resin obtained at step (a) for up to 1 hour; eluting the bound phages from the solution obtained at step c using buffer of pH ranging 1-3, and neutralizing the pH immediately after elution; amplifying the phages obtained at step d and selecting the strong interacting peptides of α-syn; performing repeated washing with the strong interacting peptides obtained at step e with Tween20 and NaCl; eluting the phages bound to α-syn obtained at step f, and identifying the peptide having Formula 1 having highest specificity to α-syn.

In another embodiment, a pharmaceutical composition comprising the peptide and a pharmaceutically acceptable excipient thereof is provided.

BRIEF DESCRIPTION OF THE DRAWINGS

Table 1 shows phage titre—5 µg of $His_6$-tagged α-syn ("His6" disclosed as SEQ ID NO: 11) was bound on $Co^{++}$-NTA resin and mentioned titre of phage library was bound to resin for 1 hour and eluted according to manufacturer's protocol. After 3 rounds of biopanning, eluted library was loaded without amplification. Individual plaques were screened from $5^{th}$ and $6^{th}$ eluent.

FIG. 4 depicts Pep.2d shows inhibition of α-syn fibrillation among different truncations. α-syn (400 µM) was incubated as mentioned above with and without Pep.2 and its derivatives and ThT fluorescence was measured after regular interval of time. As seen by lower fluorescence intensity, Pep.2d inhibits α-syn fibrillation.

MTT assay was carried out in triplicate as described in Example 6 and absorbance was measured at 570 nm to check viability of cells. Increase in absorbance in presence of Pep.2 and CycPep.2 indicated reduced α-syn associated toxicity in PC12 cells.

DETAILED DESCRIPTION OF THE INVENTION

Many of the amyloid based disorders are due to higher tendency of associated intrinsically disordered protein. One of the primary challenges in the design of therapeutics against amyloid diseases has been to develop inhibitor that could prevent the formation of amyloid fibrils. Thus, the main objective of present study is the identification of small biomolecules such as peptides that could inhibit the fibrillation of intrinsically disordered proteins.

Figure 1:
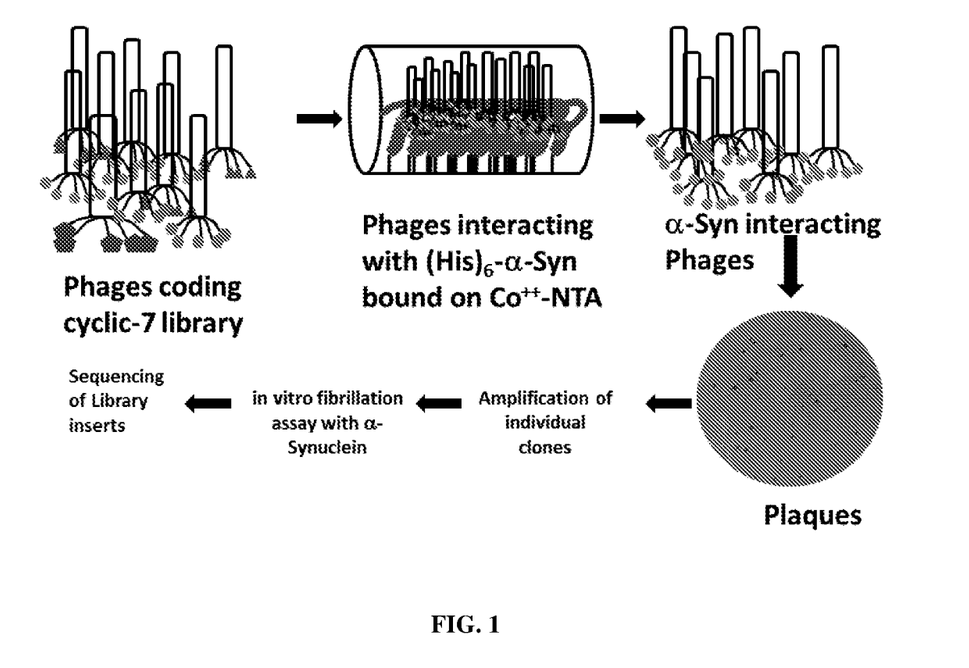
FIG. 1 depicts model describing screening of potential peptides against α-syn fibrillation using phage display library. Phage display library encoding C-7 peptides were passed through $His_6$-tagged α-syn ("His6" disclosed as SEQ ID NO: 11) bound $Co^{++}$-NTA resin. After 3 rounds of biopanning, individual interacting phages in the form of plaques were amplified and screened for inhibiting α-syn fibrillation. Potent inhibitors were sequenced and further validated by in vitro fibrillation.

Commercially available phage display library from New England Biolabs (NEB) encoding cyclic 7 peptides with phage titre $2\times10^{11}$-$7\times10^{11}$ plaque forming units (pfu), calculated as per manufacturer's protocol, was used to screen novel interacting sequences with purified α-syn as target. α-syn was quantitated using BCA protein estimation kit as per manufacturer's protocol (#23227 Thermo Scientific). Here 4-7 μg $His_6$-tagged α-syn ("His6" disclosed as SEQ ID NO: 11) was immobilized over cobalt metal affinity resin and phage library was incubated with it. FIG. 1 show the protocol used in brief Interacting peptides were selected after 5-6 rounds of biopanning, and further screened for inhibition of fibrillation assay.

Figure 2:
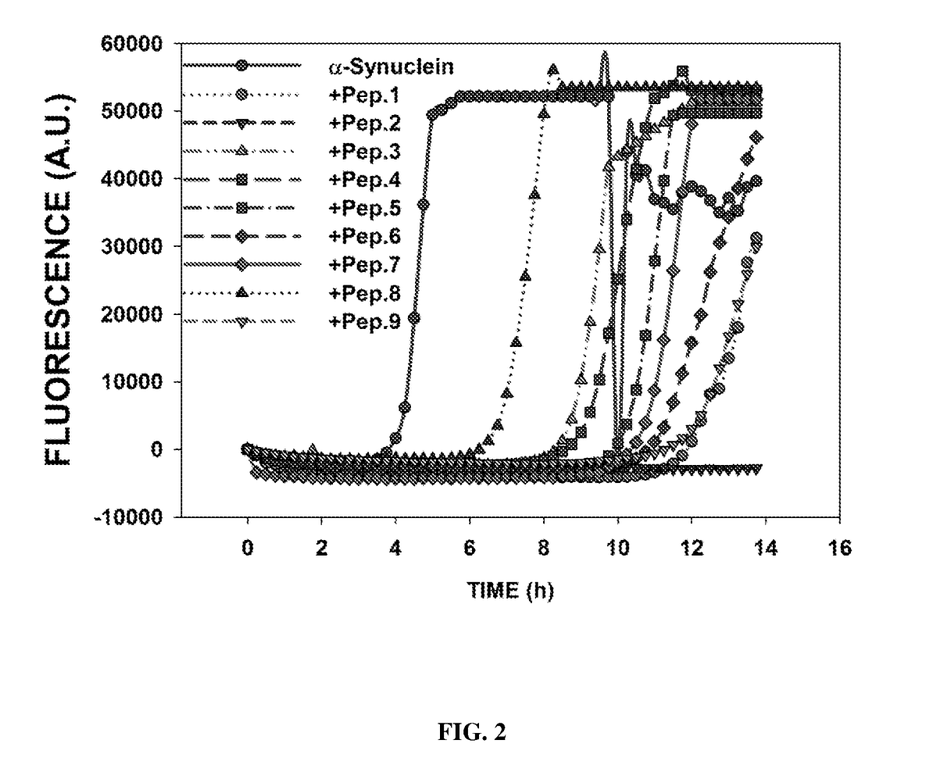
FIG. 2 depicts phage encoding Pep.3 inhibits in vitro α-syn fibrillation. Phages showing repeated binding to α-syn were further amplified according to manufacturer's protocol (NEB #E8110S). The α-syn fibrillation was carried out in the presence and absence of various screened phages. Phages inhibited α-syn fibrillation with varying efficiency. The phage encoding Pep.3 nearly completely inhibited α-syn fibrillation.

Using ThT assay, we show that α-syn, upon incubation at 37° C. under continuous shaking speed of 900 rpm forms fibrils. ThT is a fluorescent dye which is known to bind specifically to 3-sheet rich fibrils, and such binding further increases its fluorescence intensity. The fibrillation assay was carried out with α-syn in the presence and absence of above identified interacting phages. As shown in FIG. 2, different phages inhibited α-syn fibrillation to different extent. Phage encoding peptide Pep.3 was found to be most potent in inhibiting α-syn fibrillation.

Figure 3:
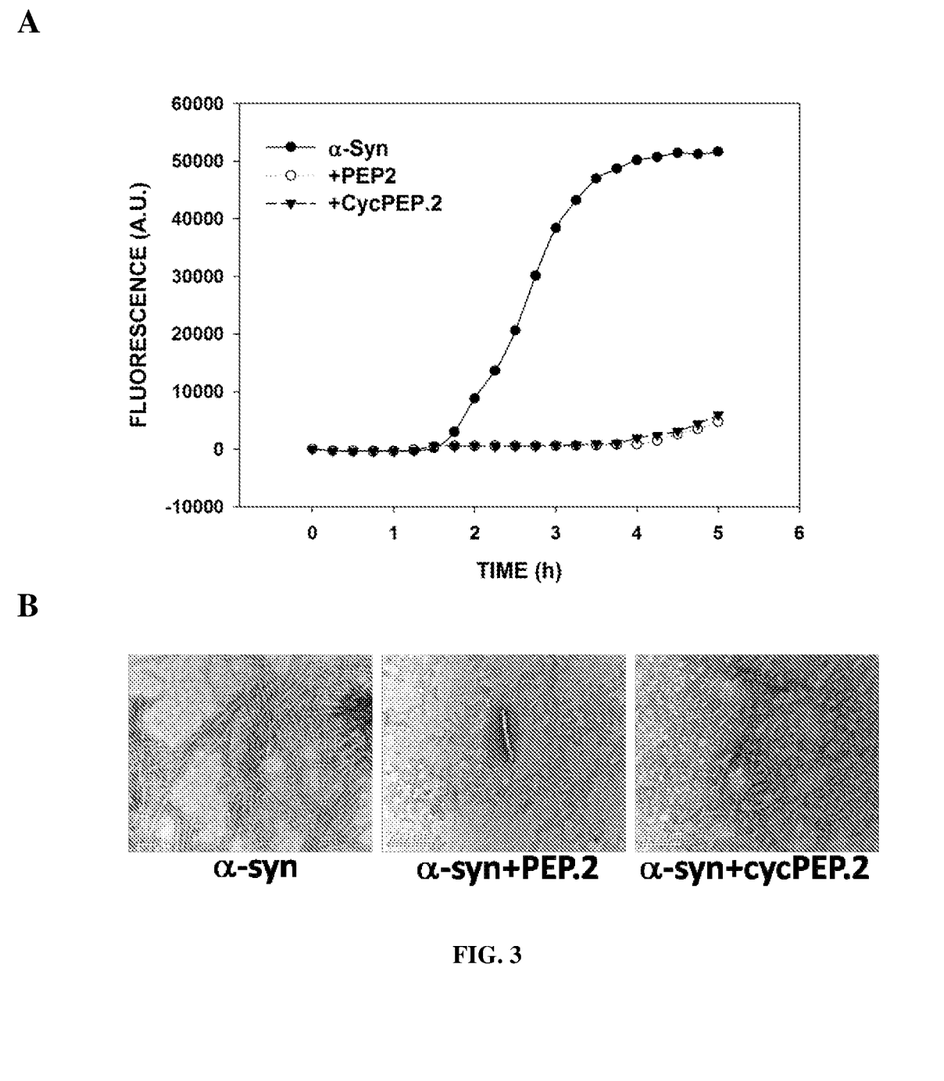
FIG. 3 shows purified Pep.3 inhibits α-syn fibrillation. (A) In vitro α-syn fibrillation assay in the presence and absence of equimolar concentrations of linear and cyclized (cycPep.3) forms of peptide Pep.3. The assay was carried out as described in Example 4. (B) TEM images from samples collected after 3 h of α-syn fibrillation in the presence and absence of Pep.3 or cycPep.3.

The genomic DNA was isolated from potential phages, and gene encoding corresponding displayed peptides were identified using DNA sequencing. The identified sequence was used to synthesize corresponding peptide. Both linear and cyclized version of peptides were synthesized. In vitro fibrillation assay was setup with linear as well as cyclic peptide. Cysteine refers to linear peptide and cystine refers to cyclic form of peptide. As evident from FIG. 3A, peptides at equimolar concentration as of α-syn were able to inhibit α-syn fibrillation. In order to further confirm that the decrease in ThioflavinT fluorescence in the presence of peptides was due to the ability of peptides to inhibit α-syn fibrillation, samples were imaged using TEM. The samples containing α-syn incubated at 37° C. in the presence and absence of equimolar concentration of peptides was collected after 5 h of fibrillation reaction, and mounted on Carbon-coated 200 mesh grids followed by visualization through Transmission Electron Microscope using phosphotungstate staining. FIG. 3B shows that the co-incubation of the peptides inhibits formation of α-syn fibrils. In the peptide, the "C" at $3^{rd}$ position and $11^{th}$ position is selected from the group consisting of cysteine and cystine respectively.

Figure 4:
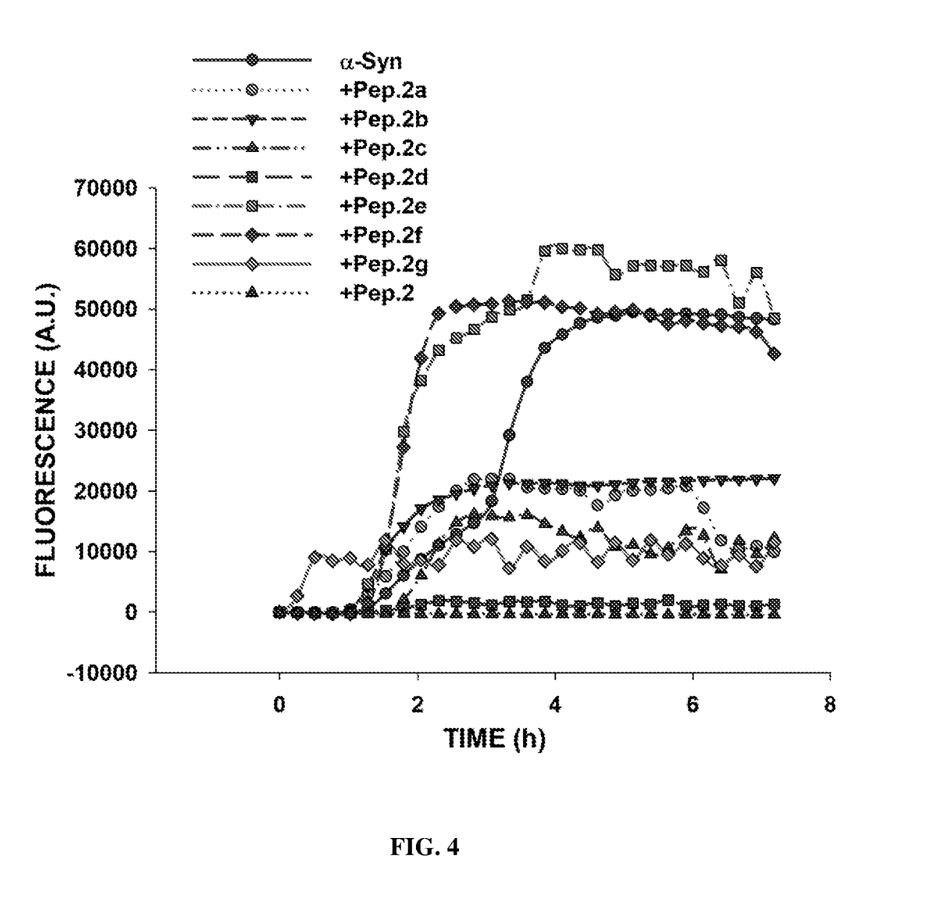

Several truncated derivatives of Pep.2 were constructed by deleting residues from N-terminal as well as C-terminal of the peptide. 7 variants of Pep.2 were commercially synthesised (GL Biochem, China) and were examined for their anti-fibrillation activity by ThT assay. Peptide variants were incubated with α-syn in equimolar concentration along with ThT. As seen in FIG. 4, the designed variants show range of inhibition activities (TABLE A). Pep.2d was able to reduce α-syn fibrillation comparable with Pep.2. Pep.2g showed approximately 80% inhibition of fibrillation.

TABLE A showing the designed variants of the peptide

| SEQ ID NOS | Internal Designation |
|---|---|
| SEQ ID NO 1 | Pep.2d |
| SEQ ID NO 2 | Pep.2 |
| SEQ ID NO 3 | Pep.2g |
| SEQ ID NO 4 | Pep.2f |
| SEQ ID NO 5 | Pep.2e |
| SEQ ID NO 6 | Pep.2c |
| SEQ ID NO 7 | Pep.2b |
| SEQ ID NO 8 | Pep.2a |

Figure 5:
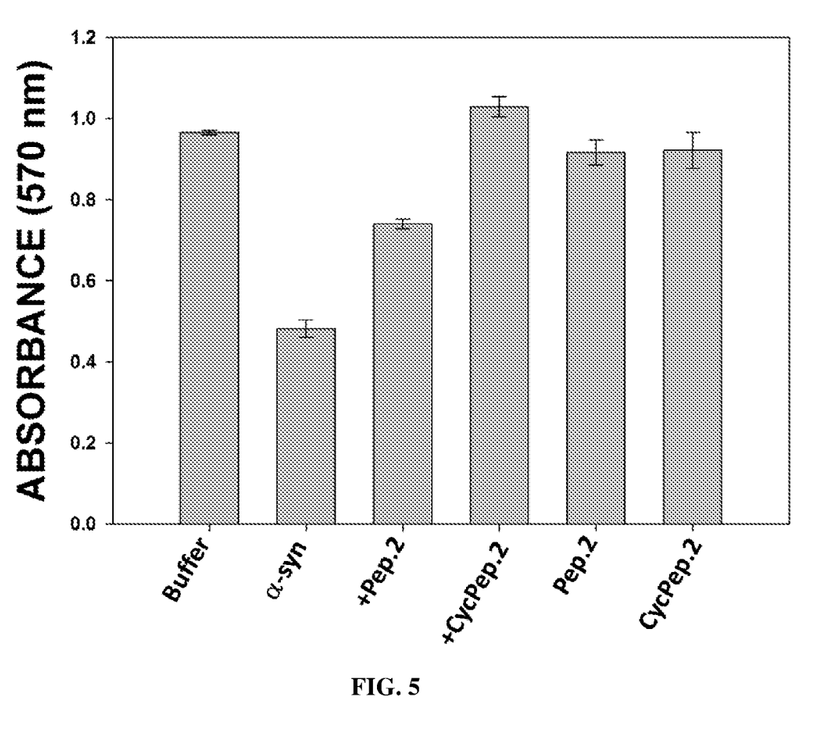
FIG. 5 depicts MTT assay with PC12 cells shows reduction in α-syn associated toxicity in presence of Pep.2 and CycPep.2. 10 µM of α-syn, with and without indicated peptides in equimolar ratio, and peptides alone were incubated with PC12 cells in 96 well plate for 24 hours. The peptides alone were taken as control to examine the toxicity of peptides to PC12 cells.

MTT ((3-(4,5-Dimethylthiazol-2-yl)-2,5-diphenyltetrazolium bromide)) cell toxicity experiments were performed using Rat phaeochromocytoma (PC12) neuronal-like cells to assess toxicity of α-syn and the protective effects of the Pep.2 and CycPep.2 generated in this study. MTT assay (FIG. 5) was performed with PC12 cells incubated with α-syn fibrillation end products in presence and absence of peptides. As seen, the presence of α-syn leads to loss of cellular viability by about 50%. However, with similar concentration of α-syn, the presence of Pep.2 and CycPep.2 improved cellular viability by 30% and >99% respectively. The peptides alone were also examined for their toxicity at even relatively higher concentration (20 mM) and as seen in the FIG. 5 peptides are not toxic to PC12 cells.

Based on the sequences obtained we undertook in-vitro fibrillation screen and the peptide having Formula no. 1: $[X_iSACX_1]_m HHHH[X_2X_3CGG]_m$ (SEQ ID NO: 9) was designed in accordance with the potent inhibitors. The above peptides can be used in pharmaceutical compositions such as lipidic formulations like liposomes, solid lipid nanoparticles with peptide stability and penetration enhancers.

EXAMPLES

The following examples are given by way of illustration therefore should not be construed to limit the scope of the Invention.

Example 1

Expression and Purification of His6-Tagged α-Syn

The N-terminal $His_6$-tagged human wild-type α-syn was expressed in *E. coli* Rossetta (DE3) (#70954 Novagen) using pET29a based expression vector. After IPTG induction bacterial cell pellets were harvested by centrifugation and resuspended in 10 mM Tris-HCl, pH 8.0, 1 mM EDTA, 1 mM Pierce protease inhibitor cocktail. Protein purification was performed with minor changes in protocol as mentioned in van Raaij et al., 2006 (van Raaij, M. E., Segers-Nolten, I. M. J., and Subramaniam, V. (2006). Quantitative morphological analysis reveals ultrastructural diversity of amyloid fibrils from alpha-syn mutants. Biophysical journal 91, L96-98). Briefly, cell lysis was carried out by sonication, lysate was boiled at 95° C. for 30 minutes, followed by centrifugation at 10,000×g for 30 minutes at 4° C. Streptomycin sulfate and Glacial acetic acid precipitated DNA was removed by centrifugation at 13,500×g for 30 minutes at 4° C. The supernatant was incubated with 50% ammonium sulfate on ice to selectively precipitate α-synuclein. The pellet was separated by centrifugation at 13,500×g for 30 min. at 4° C., and further washed with equal volume of 100 mM ammonium acetate followed by equal volume of ethanol. Pellet was dissolved in 10 mM HEPES, 50 mM NaCl, pH 7.4 and dialysed extensively to remove ammonium sulphate. Protein purity was confirmed on 15% SDS-PAGE. Protein was quantitated using BCA protein estimation kit as per manufacturer's protocol (#23227 Thermo Scientific).

Example 2

Phage Display Screening

10¹¹ titre of Phage library (#E8120S NEB) each encoding 7 residue cyclic peptide was incubated with 5 µg of His₆-tagged α-syn ("His6" disclosed as SEQ ID NO: 11) bound on Co*-NTA resin for 1 hour. Unbound phages were removed with wash buffer (150 mM NaCl, 0.02% Tween20). The bound phages were eluted using buffer of pH 2.2, and the pH was neutralized immediately after elution. Eluted library was amplified using *E. coli* ER2738 strain (#E8110S NEB). The above process was further repeated three times with eluted phages to select only strong interactors of α-syn. In 4$^{th}$ round, washing was done with 0.05% Tween20 and eluted phages were directly bound to α-syn without amplification in order to increase specificity. The process was repeated twice with eluted phages.

Example 3

Peptide Synthesis

Peptides were synthesized at peptide synthesizing facility at Institute of Microbial Technology, Chandigarh, India. Peptides were synthesized by solid phase peptide synthesis strategy using Fmoc (N-(9-fluronyl)-methoxycarbonyl) chemistry in 0.01 mmole scale on a Protein Technologies Inc, USA, PS-3 peptide synthesizer as described elsewhere (Gautam, A., Sharma, M., Vir, P., Chaudhary, K., Kapoor, P., Kumar, R., Nath, S. K., and Raghava, G. P. S. (2015). Identification and characterization of novel protein-derived arginine-rich cell-penetrating peptides, European Journal of Pharmaceutics and Biopharmaceutics 89, 93-106).

Example 4

In Vitro Fibrillation Assay

Thioflavin T (ThT) (4 mM) was added to 400 µM of purified α-syn with and without phages (10¹¹) or purified peptides at equimolar concentration in a 96 microwell plate. The plate was incubated at 37° C. with a shaking speed of 900 rpm in linear mode in a multimode plate reader (TECAN infinite M200 PRO). Fluorescence kinetics was measured after every 15 minutes with emission wavelength of 482 nm upon excitation at 442 nm. Each experiment was repeated at least three times.

Example 5

TEM Imaging

The morphology of the oligomeric species was assessed using a JEM-2100 transmission electron microscope (TEM) (Jeol, Ltd.). For TEM experiments, samples were adsorbed onto carbon-coated grids and negatively stained with 1% Phosphotungstate for 30 seconds.

Example 6

MTT Assay

MTT experiments were performed using Rat phaeochromocytoma (PC12) cells to assess cytotoxic effect of α-syn. Inhibition of PC12 cell redox activity is specific and early indicator of cell death. In MTT assay, water soluble MTT dye (3-(4, 5-dimethylthiazol-2-yl)-2,5-diphenyltetrazolium bromide) (#M2003 Sigma-Aldrich) is converted to formazan, and the conversion is monitored via absorbance measurement at 570 nm. The conversion of the MTT dye to formazan is dependent of redox status of the cell and thus the change in absorbance can be used as an indicator of the cellular viability in the assay.

PC12 cells were maintained in growth media RPMI 1640 supplemented with 10% horse serum, 5% fetal bovine serum, and antibiotics penicillin and streptomycin. The overnight grown cells (50,000 cells/well) were used for MTT assay in 96 well plate. The cells were incubated with reaction mixture (1.2 l) comprised of α-syn (400 µM) fibrils formed in the presence and absence of peptides (400 M). After incubation of 24 h at 37° C. in 5% $CO_2$ atmosphere, 10 µl of MTT (5 mg/ml in PBS) was added and incubated further for 4 h. For cell lysis, and solubilization of formazan crystal, 100 µL of the solubilization buffer (20% SDS in 50% DMF) was added to each well and incubated for 90 minutes under mild shaking conditions. The absorbance was measured at 570 nm using a multimode plate reader (TECAN infinite M200 PRO). Each experiment was performed in triplicate.

TABLE 1

| Rounds | Input Phage Titre | Wash Buffer | Eluted Phage Titre | Amplified Phage Titre |
|---|---|---|---|---|
| 1 | $10^{11}$ | 150 mM Nacl 0.02% Tween20 | $1.1 \times 10^8$ | $2 \times 10^{12}$ |
| 2 | $2 \times 10^{11}$ | 150 mM NaCl 0.02% Tween20 | $5.5 \times 10^8$ | $1.2 \times 10^{13}$ |
| 3 | $1.2 \times 10^{12}$ | 150 mM NaCl 0.02% Tween20 | $2.5 \times 10^8$ | $3.1 \times 10^{12}$ |
| 4 | $3.1 \times 10^{11}$ | 150 mM NaCl 0.05% Tween20 | $8.6 \times 10^7$ | N.A |
| 5 | $8.6 \times 10^7$ | 150 mM NaCl 0.05% Tween20 | $1.3 \times 10^5$ | N.A |
| 6 | $1.3 \times 10^5$ | 250 mM NaCl 0.05% Tween20 | $9 \times 10^3$ | N.A |

Advantages of the Invention

1. The identified peptide inhibits α-syn fibrillation and thus acts as potent therapeutics against number of neurodegenerative diseases collectively known as α-synucleinopathies.
2. As amyloid formed of diverse sequences share similar structure, identified peptides has the potential to inhibit amyloid fibril formation from other pathogenic intrinsically disordered proteins, and thus could act as potential therapeutics against various diseases such as Parkinson's Disease (PD), Alzheimer's Disease (AD), Huntington's Disease (HD), diabetes and α-synucleinopathies.

We claim:

1. A peptide for inhibition of protein aggregation having a formula of:

[X$_i$SACX$_1$]$_m$HHHH[X$_2$X$_3$CGG]$_m$ (SEQ ID NO: 10), wherein m is 1;

X$_i$ is an acetyl group;

X$_1$ is a hydrophilic polar uncharged amide group containing amino acid;

X$_2$ is His or Leu;

X$_3$ is His or Ser; and

C at the 3$^{rd}$ position and the 11$^{th}$ position is selected from the group consisting of cysteine and cystine.

2. The peptide as claimed in claim 1, wherein the C-terminus amino acid is amidated.

3. The peptide as claimed in claim 1, wherein said peptide inhibits aggregation of an amyloidogenic protein of α-synuclein.

4. The peptide as claimed in claim 1, wherein said peptide inhibits β-sheet polymerisation of amyloidogenic proteins.

5. A pharmaceutical composition comprising the peptide of claim 1 and a pharmaceutically acceptable excipient thereof.

6. A method for treating amyloid associated disorders comprising administering a therapeutically effective amount of the peptide of claim 1 to a subject with an amyloid associated disorder.

* * * * *

SEQUENCE LISTING

<160> NUMBER OF SEQ ID NOS: 12

<210> SEQ ID NO 1
<211> LENGTH: 4

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence retrieved through Sequence logo

<400> SEQUENCE: 1

His His His His
1

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence retrieved through phage display screen
<220> FEATURE:
<223> OTHER INFORMATION: N terminal acetylation
<220> FEATURE:
<221> NAME/KEY: MOD_RES
<222> LOCATION: (3)..(3)
<223> OTHER INFORMATION: cysteine or cystine
<220> FEATURE:
<221> NAME/KEY: MOD_RES
<222> LOCATION: (11)..(11)
<223> OTHER INFORMATION: cysteine or cystine

<400> SEQUENCE: 2

Ser Ala Cys Asn His His His His Leu His Cys Gly Gly
1               5                   10

<210> SEQ ID NO 3
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence retrieved through Sequence logo

<400> SEQUENCE: 3

His
1

<210> SEQ ID NO 4
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence retrieved through Sequence logo

<400> SEQUENCE: 4

His His
1

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Sequence retrieved through Sequence logo

<400> SEQUENCE: 5

His His His
1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence retrieved through Sequence logo

<400> SEQUENCE: 6

His His His His His
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence retrieved through Sequence logo

<400> SEQUENCE: 7

His His His His His His
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence retrieved through Sequence logo

<400> SEQUENCE: 8

His His His His His His His
1               5

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N terminal acetylation
<220> FEATURE:
<221> NAME/KEY: SITE
<222> LOCATION: (1)..(4)
<223> OTHER INFORMATION: This region may be present or absent
<220> FEATURE:
<221> NAME/KEY: MOD_RES
<222> LOCATION: (4)..(4)
<223> OTHER INFORMATION: hydrophilic polar uncharged amide group
      containing amino acid
<220> FEATURE:
<221> NAME/KEY: MOD_RES
<222> LOCATION: (9)..(9)
<223> OTHER INFORMATION: His or Leu
```

```
<220> FEATURE:
<221> NAME/KEY: MOD_RES
<222> LOCATION: (10)..(10)
<223> OTHER INFORMATION: His or Ser
<220> FEATURE:
<221> NAME/KEY: SITE
<222> LOCATION: (9)..(13)
<223> OTHER INFORMATION: This region may be present or absent

<400> SEQUENCE: 9

Ser Ala Cys Xaa His His His His Xaa Xaa Cys Gly Gly
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N terminal acetylation
<220> FEATURE:
<221> NAME/KEY: MOD_RES
<222> LOCATION: (3)..(3)
<223> OTHER INFORMATION: cysteine or cystine
<220> FEATURE:
<221> NAME/KEY: MOD_RES
<222> LOCATION: (4)..(4)
<223> OTHER INFORMATION: hydrophilic polar uncharged amide group
      containing amino acid
<220> FEATURE:
<221> NAME/KEY: MOD_RES
<222> LOCATION: (9)..(9)
<223> OTHER INFORMATION: His or Leu
<220> FEATURE:
<221> NAME/KEY: MOD_RES
<222> LOCATION: (10)..(10)
<223> OTHER INFORMATION: His or Ser
<220> FEATURE:
<221> NAME/KEY: MOD_RES
<222> LOCATION: (11)..(11)
<223> OTHER INFORMATION: cysteine or cystine

<400> SEQUENCE: 10

Ser Ala Cys Xaa His His His His Xaa Xaa Cys Gly Gly
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His His His His His His
1               5

<210> SEQ ID NO 12
<211> LENGTH: 6
<212> TYPE: PRT
<213> ORGANISM: Unknown
<220> FEATURE:
<223> OTHER INFORMATION: Description of Unknown: KTKEGV motif peptide
      sequence

<400> SEQUENCE: 12

Lys Thr Lys Glu Gly Val
1               5
```